United States Patent [19]

Johnson et al.

[11] Patent Number: 4,679,441
[45] Date of Patent: Jul. 14, 1987

[54] PRESSURE BALANCED LOADING PISTON FOR TRIAXIAL TEST CELLS

[75] Inventors: Christopher F. Johnson, Bountiful; Sidney J. Green, Salt Lake City, both of Utah

[73] Assignee: Terra Tek, Inc., Salt Lake City, Utah

[21] Appl. No.: 845,249

[22] Filed: Mar. 27, 1986

[51] Int. Cl.⁴ .............................................. G01N 3/10
[52] U.S. Cl. ........................................ 73/798; 73/825
[58] Field of Search ................ 73/798, 825, 807, 816, 73/837, 819, 820, 821, 822, 823

[56] References Cited

U.S. PATENT DOCUMENTS 3,975,950 8/1976 Erdei ................................ 73/819 X

FOREIGN PATENT DOCUMENTS 813186 3/1981 U.S.S.R. ............................... 73/825

Primary Examiner—Jerry W. Myracle
Attorney, Agent, or Firm—M. Reid Russell

[57] ABSTRACT

A triaxial test cell and pressure balanced piston therefor that includes a housing containing a vessel wherein a test specimen is located, immerged in a confining fluid. The housing includes a passage wherein the piston is installed to slide so as to move an end thereof into the vessel, which passage includes an annular area formed intermediate therealong wherein a collar portion of the piston is fitted. The piston collar portion includes a face whose surface area is equal to the area of the piston end face that travels into the vessel, and the annular area above that collar upper face is connected by an open passage to that vessel. The piston and passage include appropriate ring seals for providing a pressure seal above and below the passage annular area and that annular area is separated by a pressure seal arranged around the piston collar, with the annular area below that collar vented to atmosphere.

9 Claims, 2 Drawing Figures

PRESSURE BALANCED LOADING PISTON FOR TRIAXIAL TEST CELLS

BACKGROUND OF THE INVENTION

1. Field of the Invention

This invention relates to materials testing apparatus, specifically, test cells for testing a specimen of material along three orthogonal axes.

2. Prior Art

For many materials such as rocks, salt, ice, concrete and the like it is important to measure a variety of properties under a triaxial state of stress, where the stresses act simultaneously along three orthogonal axes of the specimen. Such tests are conducted in a pressure vessel of the triaxial test cell that contains the specimen and a confining fluid and receives a piston to extend into that vessel. In such triaxial test cell, the vessel is typically narrow and can be open to admit the specimen and confining fluid. A piston is arranged to travel into the vessel from a cylindrical passage adjacent the test cell vessel. The piston compresses the fluid surrounding the specimen, applying the required triaxial hydrostatic stress thereto. In such arrangement, an axial loading force is applied to the loading piston that moves into the test cell vessel, pressurizing the confining fluid that applies a deviatoric axial stress to that test specimen, which stress is greater than a hydrostatic or reactive stress exerted by the pressurized fluid.

The above arrangement for applying the required deviatoric stress to the specimen has two drawbacks. Specifically, as the piston advances into the triaxial test cell, the pressurized fluid is further compressed, thus increasing the reactive fluid pressure when indeed it might be desirable to maintain confining pressure constant during a test; and, in order to apply the deviatoric stress to that test specimen, the actual force on the piston must be greater than the reactant force produced as the confining fluid acts on the cross sectional area of the piston face. The present invention, by providing a pressure balanced piston minimizes the magnitude of the external axial force required to generate a specified deviatoric stress in the test specimen.

Heretofore, to apply deviatoric stresses to a test specimen in a triaxial test cell the reactive force of the confining fluid had to be taken into account. The stepped piston and channeling arrangement of the present invention provides for a balancing where the force exerted by the confining fluid that is resistive to piston travel therein is cancelled.

SUMMARY OF THE INVENTION

It is a principal object of the present invention in a pressure balanced loading piston for a triaxial test cell arrangement to minimize the external force required to generate a specific deviatoric stress on a test specimen subjected to confining pressure in a fluid containing a triaxial test cell.

It is another object of the present invention to provide a balanced piston arrangement such that moving the piston into or out of the test cell will not disturb the confining pressure in the test cell, allowing the continuing pressure to be controlled completely independently of axial piston travel.

It is another object of the present invention to provide a balanced piston arrangement for a triaxial test cell that provides for a cancellation of a reactive force produced in a confining fluid in the test cell when the piston is moved into that fluid whereby the deviatoric stresses exerted on a test specimen in that fluid can be directly calculated from the force applied to move that piston and piston area only.

Still another object of the present invention is to provide a balanced loading piston for use with a triaxial test cell that is easy and inexpensive to construct.

The present invention in a pressure balanced loading piston for a triaxial test cell includes a loading piston and arrangement for applying an axial loading force at one end thereof to urge the piston to extend into a fluid filled chamber of the test cell wherein a test specimen is located. The loading piston includes centrally and coaxially therewith an outwardly extending stepped or collar portion that preferably extends at a normal or right angle outwardly from the piston longitudinal surface whose upper and lower surface faces are generally equidistant from that piston surface and are parallel to one another, encircling the piston. To provide a balanced piston the area of the upper piston collar portion face is equal to the cross section area of the piston end that travels into the fluid containing vessel of the test cell. To accomodate the piston the test cell includes a cylindrical opening or passage from the confining fluid vessel to without the test cell that incorporates an annular area intermediate that passage wherein the piston collar is fitted. The collar divides that annular area into upper and lower portions, and the upper portion is connected by a fluid carrying line to the vessel to allow a free flow of fluid therebetween. The piston includes a pressure seal arranged centrally around the collar portion that seals against the annular area wall to prohibit fluid flow between the upper and lower portions thereof of the cylindrical opening. The lower portion of that annular area below the collar is vented to atmosphere. Pressure seals are arranged in the cylindrical opening walls above the annular portion to engage the piston surface. The lower pressure seal prohibits flow from the test cell vessel into the annular area below the piston collar, and the upper pressure seal restricts fluid flow from that annular area above the collar to without the test cell. The fluid passage loop that connects the vessel to the upper annular portion is preferably within the test cell and is open to allow the vessel confining fluid to flow freely therebetween. Additionally, a pressure control device is connected to the test cell vessel for controlling the fluid pressure within that vessel.

For a balanced loading, the piston pressure collar surface area at its upper face is equal to the cross sectional area of the piston face that enters the triaxial test cell. With a free flow of confining fluid between the vessel and annular area opposite to that collar upper face, the pressure in that confining fluid will be equal and opposite to the force exerted against the entry of that piston end face into the confining fluid, the forces thereby cancelling each other out. So arranged, the movement of the piston face into or out of the confining fluid will not alter the confining pressure within the test cell.

BRIEF DESCRIPTION OF THE DRAWING

These and other objects and features of the present invention in a pressure balanced loading piston for a triaxial test cell will become more fully apparent from the following description in which the structure of the invention is described in detail in conjunction with the accompanied drawings.

DETAILED DESCRIPTION

Referring Now to the Drawings

Figure 1:
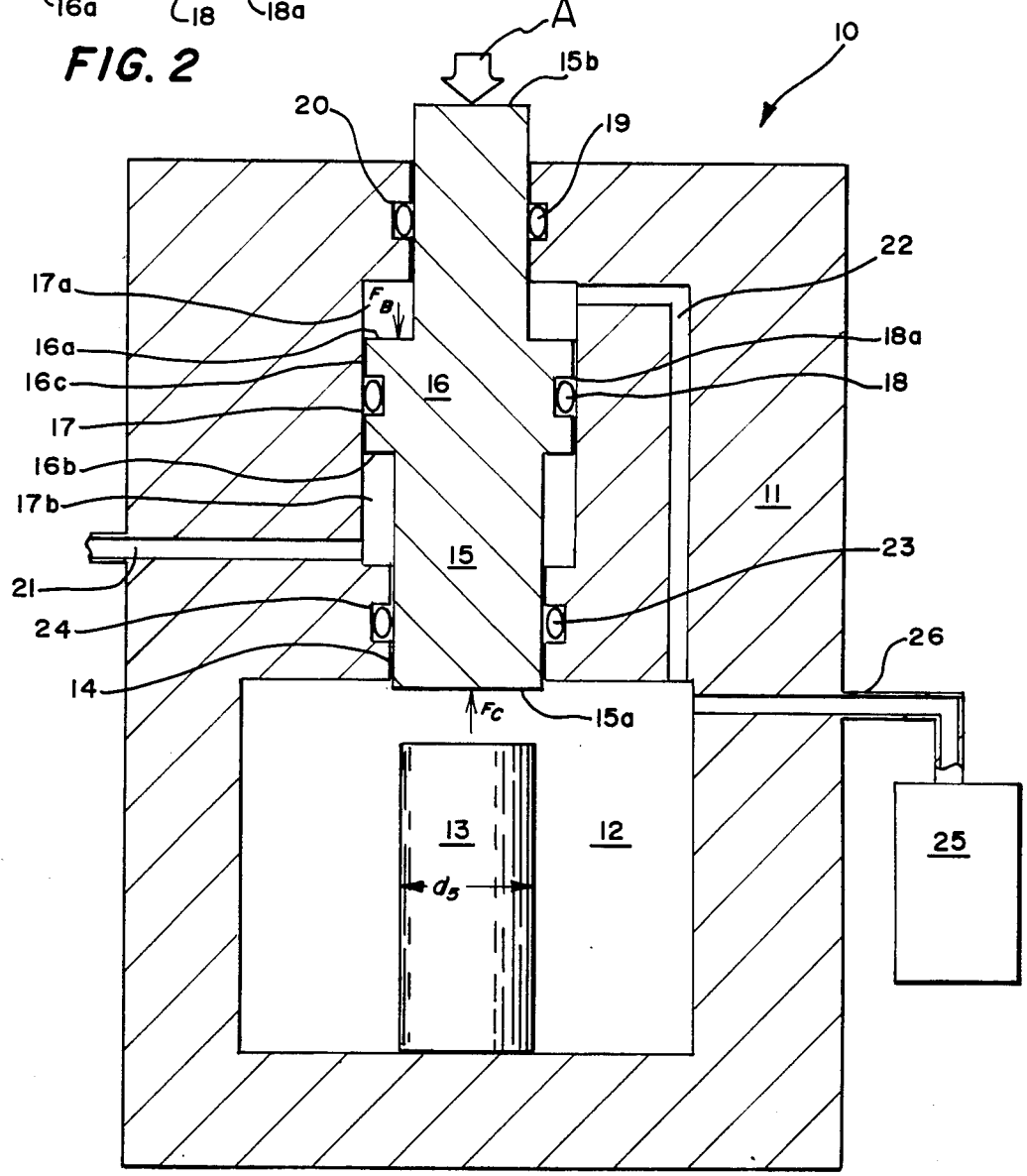
FIG. 1 is a side elevation sectional view of a schematic of a triaxial test cell showing the test cell as including a vessel wherein a confining fluid is maintained and shows a test specimen positioned therein and a piston that includes a collared portion therearound that is arranged to travel within a cylindrical opening through that test cell to extend into that vessel, and shows appropriate pressure seals and the cylindrical opening as including an annular portion below the piston collar that is open to atmosphere with the annular section above the collar linked by an open passage to the test cell vessel.

FIG. 1 shows a longitudinal sectional view of a preferred triaxial test cell of the present invention hereinafter referred to as test cell 10. The test cell includes a housing 11 that it should be understood consists of a number of sections that are joined and maintained together, by conventional fasteners. For convenience, the different sections and their connection arrangement have not been shown nor has an arrangement for providing access into a vessel 12 that, it should be understood, is included with the test cell. While not specifically shown, the test cell 10, it should be understood, includes various compartments arranged therein that can be taken apart so as to allow access to the vessel 12 to position therein a specimen 13 of a diameter $d_s$ that is to be subjected to triaxial or deviatoric axial stress loading.

The vessel 12 of the test cell 10 is provided to contain a confining fluid that can be conveniently drained to provide access therein as by opening fasteners, not shown, and appropriately breaking apart the test cell housing 11 for positioning and removal of test specimen 13. The vessel 12 is open to a cylindrical opening 14 of an upper portion of housing 11. The test specimen 13 is to be positioned opposite to opening 14, and a loading piston 15 is arranged to travel within that cylindrical opening, a face 15a thereof moving into that vessel 12 against a confining fluid therein.

Figure 2:
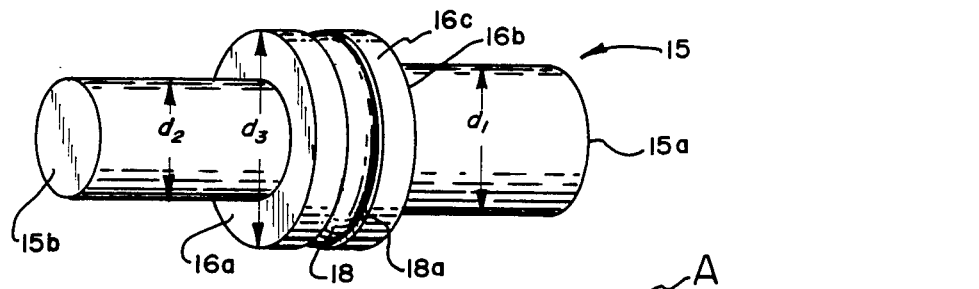
FIG. 2 is a perspective view of the piston of FIG. 1 that has been removed from the triaxial test cell.

The piston 15 is shown in FIG. 2 removed from the test cell housing 11, a lower end, across face 15a thereof, shown to have a diameter $d_1$. The piston upper portion is shown to have a diameter $d_2$ across an end face 15b, and a stepped or collar portion 16 is shown to have a face adjacent to the piston upper portion and has a diameter $d_3$. The diameters $d_1$ and $d_2$ are shown to be different in FIG. 1, but, it should be understood, they can be the same within the scope of this disclosure.

FIG. 1 shows a loading force, as arrow A, being applied against piston face 15b to urge the piston opposite end into the vessel 12 of test cell housing 11. In such operation the housing is generally held stationary as the loading force is applied to piston 15. Shown in FIGS. 1 and 2 the piston 15 includes the stepped or collar portion 16 that is coaxial to and preferably projects at a normal or right angle out from the piston surface and includes upper and lower faces 16a and 16b that are preferably parallel to one another, and are preferably equal in radius to terminate in a right angle surface therebetween 16c, which surface 16c is preferably parallel to the piston surface. The area of piston collar lower face 16b is not a factor in operation of the test cell. The collar 16 is arranged to travel within an annular portion 17 of the cylindrical opening 14. The piston collar surface 16c thereby travels along the surface of annular portion 17 and includes a pressure seal 18 that is fitted into a channel 18a formed therearound, which pressure seal 18 engages and forms a seal with the wall of annular portion 17. So arranged, the annular portion 17 is divided by the piston collar 16 into an upper section 17a that is closed by the collar upper face 16a and a lower section 17b that is closed by the collar lower face 16b.

The lower section of the annular portion 17b is open to atmosphere through a line 21 that extends to without the test cell body 11. The integrity of the upper section 17a is maintained by pressure seal 19 that is fitted with a groove or channel 20 formed within and around the cylindrical opening 17. The pressure seal 19 is to engage the piston upper portion surface sealing thereagainst. The annular portion upper section 17a is therefore isolated between the sealing rings 18 and 19. This upper section 17a is connected through a line 22 to the vessel 12 that is arranged to freely pass fluid therebetween. The pressure integrity of the vessel 12 to the annular portion lower section 17b is maintained by a pressure seal 23 that is arranged in a channel 24 formed around the wall of cylindrical opening 17. Pressure seal 23 engages the surface of the lower portion of piston 15 above face 15a thereof. A pressure control device 25 is shown connected through line 26 into the test cell vessel 12 that is for controlling confining pressure.

Written mathematically, for an unbalanced piston that would be typical for an earlier triaxial test cell, deviatoric stress applied to a test specimen was found as follows:

$$\sigma_D = \frac{F_A - P_C \left(\frac{\pi}{4}\right) (D_P)^2}{\left(\frac{\pi}{4}\right) (D_S)^2} \quad (1)$$

where
$\sigma_D$ = Deviatoric stress applied to the test specimen.
$F_A$ = External axial load applied to the loading piston.
$P_c$ = Pressure of the confining fluid.
$D_P$ = Diameter of the loading piston.
$D_s$ = Diameter of the test specimen.

Additionally, to restrict the piston 15 from moving out of the test cell housing 11, a minimum external force had to be applied, as shown by the formula:

$$F_{Amin} = P_C \left(\frac{\pi}{4}\right) (D_P)^2 \quad (2)$$

From the above, it is clear that former triaxial test cells employing a uniform diameter piston have suffered from two problems: (1) the axial force applied to the piston has to be greater than the reactive force created by the pressure of the confining fluid so as to avoid the piston being moved oppositely to the applied axial force; and (2) piston travel into a confining fluid produces a change in the confining pressure in the triaxial test cell.

With the pressure balanced piston of the present invention the two problems set out above are solved. As shown in FIG. 1, a free flow of the confining fluid is provided through passage 22 and the areas of piston face 15a and the collar upper face 16a have the same force or stress exerted thereon by that fluid. The force exerted on the collar upper face 16a, shown as arrow $F_B$, will be equal and opposite to the reactive force of the confining fluid pressure, shown as arrow $F_C$, that acts against travel of the piston face 15a into the confining fluid. With the cross sectional areas $$\frac{\pi}{4} d_1^2 \text{ and } \frac{\pi}{4} (d_3 - d_2)^2,$$

of the collar upper face 16a and piston face 15a equal, a pressure balancing will exist such that the applied external load, arrow A, will be the deviatoric load applied to the test specimen 13 and therefore the reactive force of the confining fluid pressure need not be considered. This force is represented by the equation:

$$F_C = P_C \times A_P \text{ where } A_P = \frac{\pi}{4} d_1^2 \qquad (3)$$

Summarizing, a utilization of the pressure balanced loading piston of the present invention with a triaxial test cell provides for a generation of a required deviatoric stress with an expenditure of a smaller external axial load or force than has been heretofore possible. With the balanced piston it is not necessary to take into account or to overcome the reactive pressure exerted by the confining fluid generated by piston movement into the test cell vessel. A second advantage of the pressure balanced loading piston 15 over earlier arrangements is that the pressure within the confining fluid will not be changed during the test. Fluid displaced by the advancing of the piston face 15a into the vessel 12 is exactly equal to and of opposite effect to fluid traveling into the annular upper section 17a above piston collar face 16a. In a test, the volume change in the test chamber 12 will exactly equal a volume gain in the annular upper section 17a and no pressure prepurabation will be introduced through the confining fluid due to that piston travel. A lessor requirement for pressure control in the confining fluid is thereby provided in a test where constant confining pressure is desired. Of course, it is desirable to monitor the pressure within the confining fluid to avoid an over pressurizing that could disrupt pressure seal integrity.

The above discussion has been directed to a balanced piston arrangement where the areas of the respective piston end face 15a and collar upper face 16a are equal. It should, however, be understood, within the scope of this disclosure, that the respective faces could be formed to have different areas to provide an unbalanced piston. Such unbalancing could be provided to compensate for seal friction or to create a specific preload in the test cell.

Hereinabove has been described a preferred embodiment of the pressure balanced loading piston of the present invention and its use in a triaxial test cell. It should be understood that the description is made by way of example only and that any changes can be made thereto without departing from the subject matter coming within the scope of the following claims, which claims we regard as our invention.

We claim:

1. A triaxial test cell and piston therefor comprising a triaxial test cell housing containing a vessel arranged to provide for receipt and removal of a specimen of material to be tested and to maintain a confining fluid therein, the housing including a cylindrical opening into said vessel that receives a piston slidably fitted therein, said cylindrical opening to include an intermediate enlarged annular portion; a piston for sliding installation within said cylindrical opening, said piston including, intermediate therealong, a collar formed to extend outwardly from the piston longitudinal surface that includes upper and lower faces; fluid passage means connecting said vessel to the cylindrical opening annular portion above said collar upper face for freely passing confining fluid therethrough; means for venting to atmosphere the cylindrical opening annular portion below said collar lower face; and seal means arranged to prohibit passage of confining fluid into said cylindrical opening annular portion below said piston collar lower face and from said cylindrical opening annular portion above said piston collar upper face to without the test cell.

2. A triaxial test cell and piston as recited in claim 1, wherein the collar upper face furthest from the vessel has a surface area that is equal to the surface area of the face of the piston that travels into said vessel.

3. A triaxial test cell and piston as recited in claim 1, wherein the collar upper face furthest from the vessel and the face of the piston that travels into said vessel have a selected area relationship that takes into account seal friction or to establish a preload condition such that a resultant pressure produced by piston travel into said vessel will balance with the load applied on said collar upper face.

4. A triaxial test cell and piston as recited in claim 1, wherein the fluid passage means is arranged within the triaxial test cell housing.

5. A triaxial test cell and balanced piston as recited in claim 1, wherein the pressure seal means are individually arranged between the piston surface and the wall of the cylindrical opening above and below the piston collar and between the surface of the piston collar and the wall of the cylindrical opening annular portion.

6. A pressure balanced piston for a test cell that includes a vessel wherein a specimen is to be positioned, which vessel receives a confining fluid and includes a cylindrical opening that intercepts said vessel that is to receive the pressure balanced piston fitted in sliding engagement therein, the improvement comprising a collar formed intermediate from and around the piston longitudinal surface, the collar to include a face that is parallel to and distant from the piston end that travels into the test cell vessel; an annular portion formed intermediate the cylindrical opening to accomodate said collar of said piston positioned to slide therealong; means for providing unobstructed passage of confining fluid from said vessel to said cylindrical opening annular portion opposite said piston collar face; and means for venting to atmosphere the cylindrical opening annular portion below said piston collar.

7. A pressure balanced piston as recited in claim 6, wherein the collar face furthest from the vessel has a surface area that is equal to the surface area of the face of the piston that travels into said vessel.

8. A pressure balanced piston as recited in claim 6, wherein the collar face furthest from the vessel and face of the piston that travels into said vessel have a selected area relationship that takes into account seal friction or to establish a preload condition such that a resultant pressure produced by piston travel into said vessel will balance with the load applied on said collar upper face.

9. A pressure balanced piston as recited in claim 6, wherein the piston collar includes equal and parallel upper and lower faces.

* * * * *